(12) United States Patent
Greenway et al.

(10) Patent No.: US 7,433,025 B2
(45) Date of Patent: Oct. 7, 2008

(54) AUTOMATED PROTEIN CRYSTALLIZATION IMAGING

(75) Inventors: Bryan Greenway, Franklin, TN (US); Dave Riling, Franklin, TN (US)

(73) Assignee: Thermo Fisher Scientific (Asheville) LLC, Asheville, NC (US)

( * ) Notice: Subject to any disclaimer, the term of this patent is extended or adjusted under 35 U.S.C. 154(b) by 337 days.

(21) Appl. No.: 10/480,477

(22) PCT Filed: Apr. 10, 2003

(86) PCT No.: PCT/US03/10954

§ 371 (c)(1), (2), (4) Date: Feb. 11, 2005

(87) PCT Pub. No.: WO03/087326

PCT Pub. Date: Oct. 23, 2003

(65) Prior Publication Data

US 2005/0117144 A1 Jun. 2, 2005

Related U.S. Application Data

(60) Provisional application No. 60/371,115, filed on Apr. 10, 2002.

(51) Int. Cl.
*G01N 21/00* (2006.01)
(52) U.S. Cl. .......................................... 356/30
(58) Field of Classification Search ............... 356/30
See application file for complete search history.

(56) References Cited

U.S. PATENT DOCUMENTS

| 6,407,373 | B1 | 6/2002 | Dotan |
| 6,449,088 | B1 | 9/2002 | Pettingell et al. |
| 6,621,275 | B2 | 9/2003 | Cotton et al. |
| 6,628,381 | B1 | 9/2003 | Komem et al. |
| 7,108,970 | B2 * | 9/2006 | Levinson ................. 435/6 |
| 2003/0118800 | A1 * | 6/2003 | Thomas et al. .......... 428/215 |

* cited by examiner

*Primary Examiner*—Tarifur Chowdhury
*Assistant Examiner*—Tara S Pajoohi
(74) *Attorney, Agent, or Firm*—Baker & Hostetler LLP

(57) ABSTRACT

An apparatus that automatically captures, stores and analyzes images of crystallization experiments contained in a number of crystallization plates. The apparatus includes a plate nest capable of accommodating protein crystallization plates of a plurality of different types, image acquisition optics, including an objective lens and an image capturing device, for focusing an image of a crystallization well, a light source including a bright field illumination device and a dark field illumination device, a nest positioning controller for moving the position of the plate nest with respect to the image acquisition optics to align various selected wells with said objective lens for imaging of the content of the wells. A database stores experiment information associated with each of the crystallization plates, the experiment information including identification of specific crystal forming parameter values, each of the crystallization plates is identified in said database by a unique identification code. A crystallization imaging controller controls crystallization imaging by retrieving the experiment information for each crystallization plate inserted into the apparatus, and controlling the nest positioning controller and the image acquisition optics in accordance with the retrieved experiment information. The apparatus captures multiple images of each crystal site using different light source and polarization conditions, and processes the multiple images to form extended fused images of each crystal site.

25 Claims, 26 Drawing Sheets

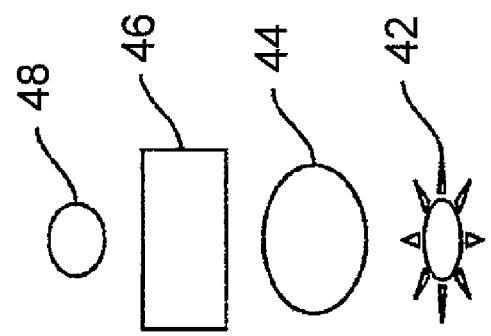

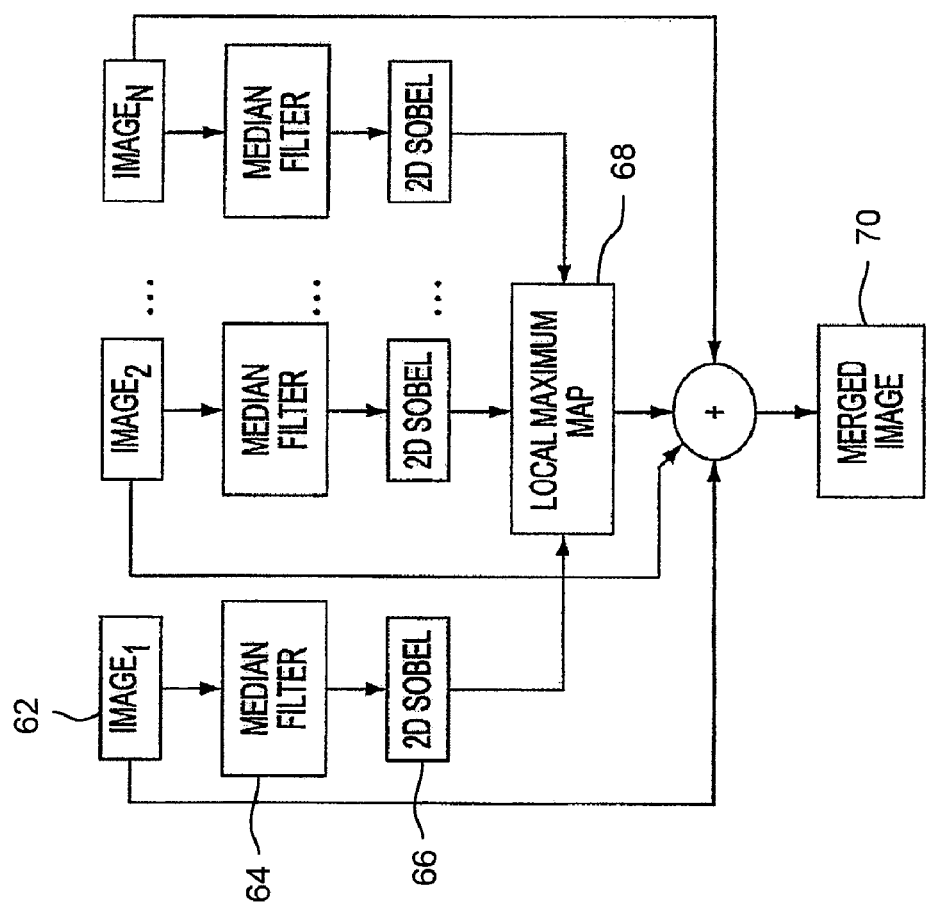

AUTOMATED PROTEIN CRYSTALLIZATION IMAGING

CROSS-REFERENCE TO RELATED APPLICATION

The present application claims priority under 35 U.S.C. § 119(e) of provisional application Ser. No. 60/371,115, filed Apr. 10, 2002, and incorporated herein by reference in its entirety.

BACKGROUND OF THE INVENTION

The present invention relates generally to the field of protein crystallization analysis and in particular to a process and apparatus for capturing, indexing, analyzing and storing images of protein crystallization samples.

Protein crystallization is a technique used to analyze the molecular structure of proteins. In this technique, varying controlled ratios and combinations of certain chemical reactants or catalysts are added to a protein sample or "drop" to induce the protein to crystallize so that its structure may be analyzed for use in biochemical research applications.

As shown in FIG. 1, one type of crystallization plate 2 includes a number of cells, each cell 4 having a number of satellite wells (three in the example). The cells are identified by row and column number, such as A1, B10, etc., and each satellite well is identified by its position number in the cell (such as 1, 2 or 3). A quantity of a protein is placed into each of the satellite wells, and a different experimental amount of a crystallization catalyst is added to each satellite well in an attempt to induce crystallization of the protein. The mixture is given a sufficient time to react, and then the satellite wells must be viewed under a microscope to determine if sufficient crystallization has occurred. The particular amounts and/or ratios of crystallization catalyst material and protein placed in each satellite well must be recorded in order to determine which ratios and combinations are successful in producing crystallizations. Typically, one protein will be used for each plate, and different catalysts and ratios of catalysts will be added to the protein drops in each satellite well.

Achieving successful protein crystallization is very time consuming and tedious, as only a very small number of crystallizations of a protein occur for many tens or hundreds of thousands of experimental reactant ratios and combinations. Additionally, the contents of a well may be more complex than a simple crystal structure. Specifically, the protein sample (drop) may be turbid as opposed to clear, there may be micro-crystal fields in the sample, protein may be aggregated, and crystals may be embedded in a precipitate field. Since each of these possibilities requires specialized lighting conditions in order to be detected, it is necessary to take many different pictures of the same well under different lighting and focus conditions, thus adding even more complexity to the analysis process.

Accordingly, there is a need for improvement in obtaining, analyzing, and storing protein crystallization experiment images whereby all potential information in an experiment well can be captured quickly and efficiently, and stored together with all experimental parameters and conditions associated with the well.

SUMMARY OF THE INVENTION

According to a preferred embodiment of the invention, an apparatus is provided that automatically captures, stores and analyzes images of crystallization experiments contained in a plurality of crystallization plates, the apparatus including a plate nest capable of accommodating protein crystallization plates of a plurality of different types, the plates each including a plurality of crystallization wells each including a particular crystallization experiment, image acquisition optics, including an objective lens and an image capturing device, for focusing an image of a crystallization well positioned under the objective lens and electronically capturing the focused image, a light source including a bright field illumination device and a dark field illumination device, each of the bright field and dark field illumination devices being independently energized to introduce light into a crystal image well to enable capture of separate bright field and dark field images of the crystal image well by the image acquisition optics, a nest positioning controller for moving the position of the plate nest with respect to the image acquisition optics to align various selected wells with the objective lens for imaging of the content of the wells, a database for storing experiment information associated with each of the plurality of crystallization plates, the experiment information including identification of specific crystal forming parameter values, and wherein each of the plurality of crystallization plates is identified in the database by a unique identification code, and a crystallization imaging controller for controlling crystallization imaging by retrieving the information for each crystallization plate inserted into the apparatus, and controlling the nest positioning controller and the image acquisition optics in accordance with the retrieved experiment information.

According to another aspect of the invention, the imager apparatus obtains and stores multiple images of each desired crystallization well under a number of different lighting and/or focusing conditions, and processes the multiple images to form a fused image containing all available information pertaining to a crystal image well.

BRIEF DESCRIPTION OF THE DRAWINGS

FIG. 4 is a diagram showing the use of polarization filters in combination with a light source according to another aspect of the invention;

FIG. 6 is a flow diagram of one embodiment of a process for obtaining the merged extended focus image of FIG. 5b according to the present invention;

DETAILED DESCRIPTION OF THE PREFERRED EMBODIMENTS

The present invention will now be described in conjunction with the accompanying drawings. However, it will be understood that the following detailed description is for purposes of providing an explanation and disclosure of the concepts of the invention only, and is not intended to define the scope of the invention, which is defined solely by the claims.

Figure 8:
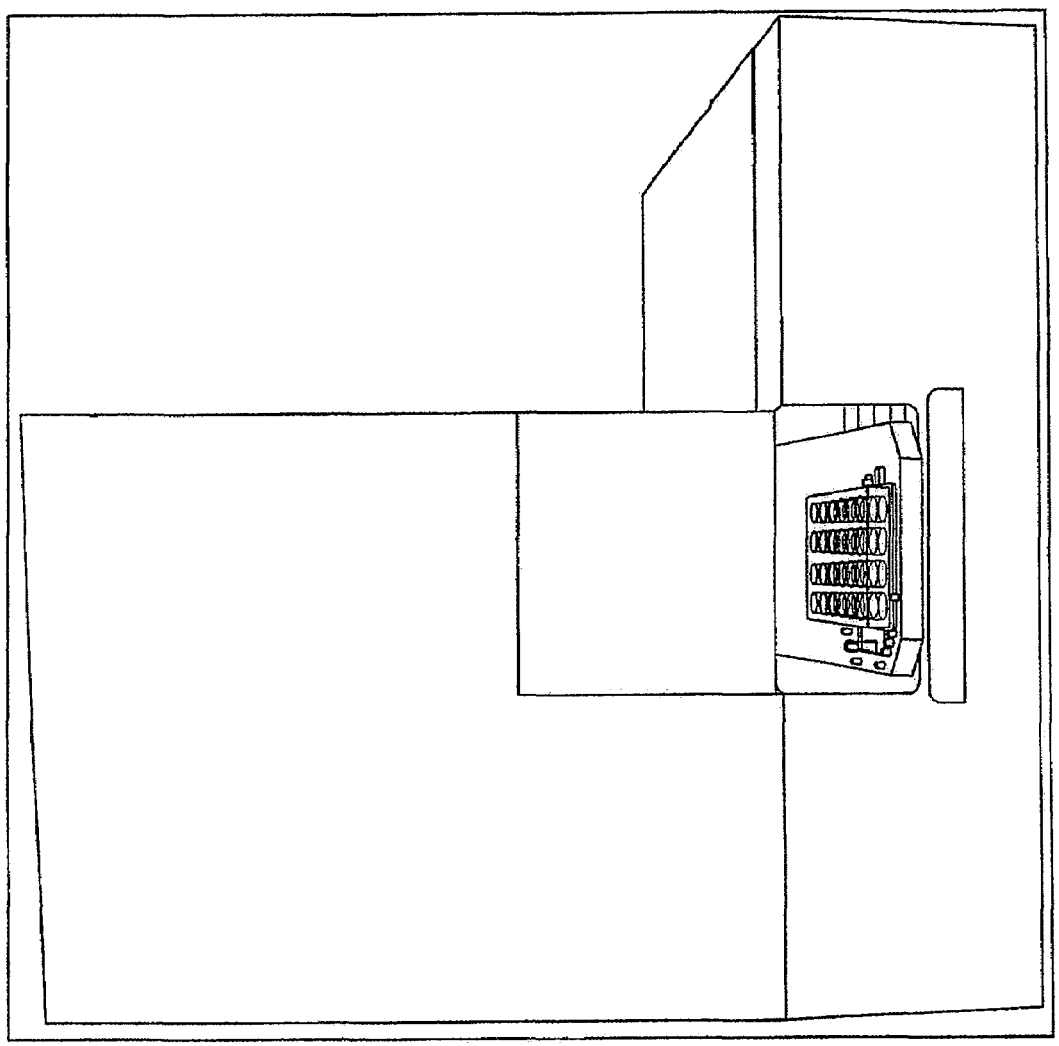
FIG. 8 is a perspective view of an imager housing showing a plate inserted into a plate nest holder according to one embodiment of the invention.

The imager has a plate nest or holder, as shown in FIG. 8, which extends to a load/unload position via a servo controller as shown, to permit an imaging plate to be loaded into the nest for imaging, and to be removed from the nest after image processing is completed. The loading and unloading of the plates may be performed manually, or via robotics from a plate storage area. Each plate is labeled with a bar code label containing a unique identification code, which allows automatic identification of each plate through scanning of the bar code label by a bar code scanner. After a plate is loaded, the nest is retracted into the imager for image processing.

The imager has the ability to be run in one of three modes: automatic, semi-automatic, or manual. In automatic mode, each plate is imaged predicated on the image mask parameters selected by the user on a GUI (graphical user interface, see FIG. 25) during a plate setup phase. An image mask is the marking of the wells from which images are desired.

Figure 1:
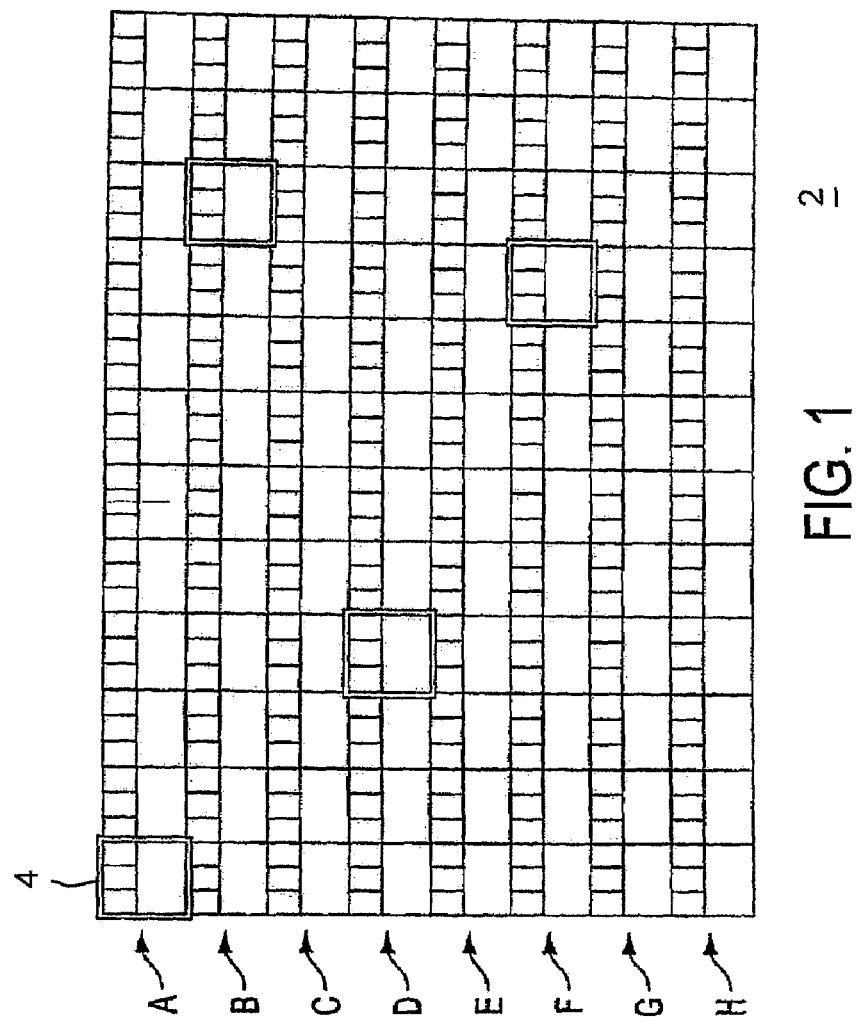
FIG. 1 is a diagram of a protein crystallization plate for use in an imager according to the present invention.

In the example plate shown in FIG. 1, cells A1, B10, D4 and F9 are marked by the user to be imaged. Each cell of the plate contains three satellite wells. The satellite or sitting drop well is selected based on its position (1, 2, and/or 3 in this example). Depending on which satellite well setting is desired, the imager will automatically acquire images for the selected wells per the preselected satellite well selection. Once all images have been captured the nest is extended to the load/unload position located outside of the main housing, as shown in FIG. 8.

Figure 25:
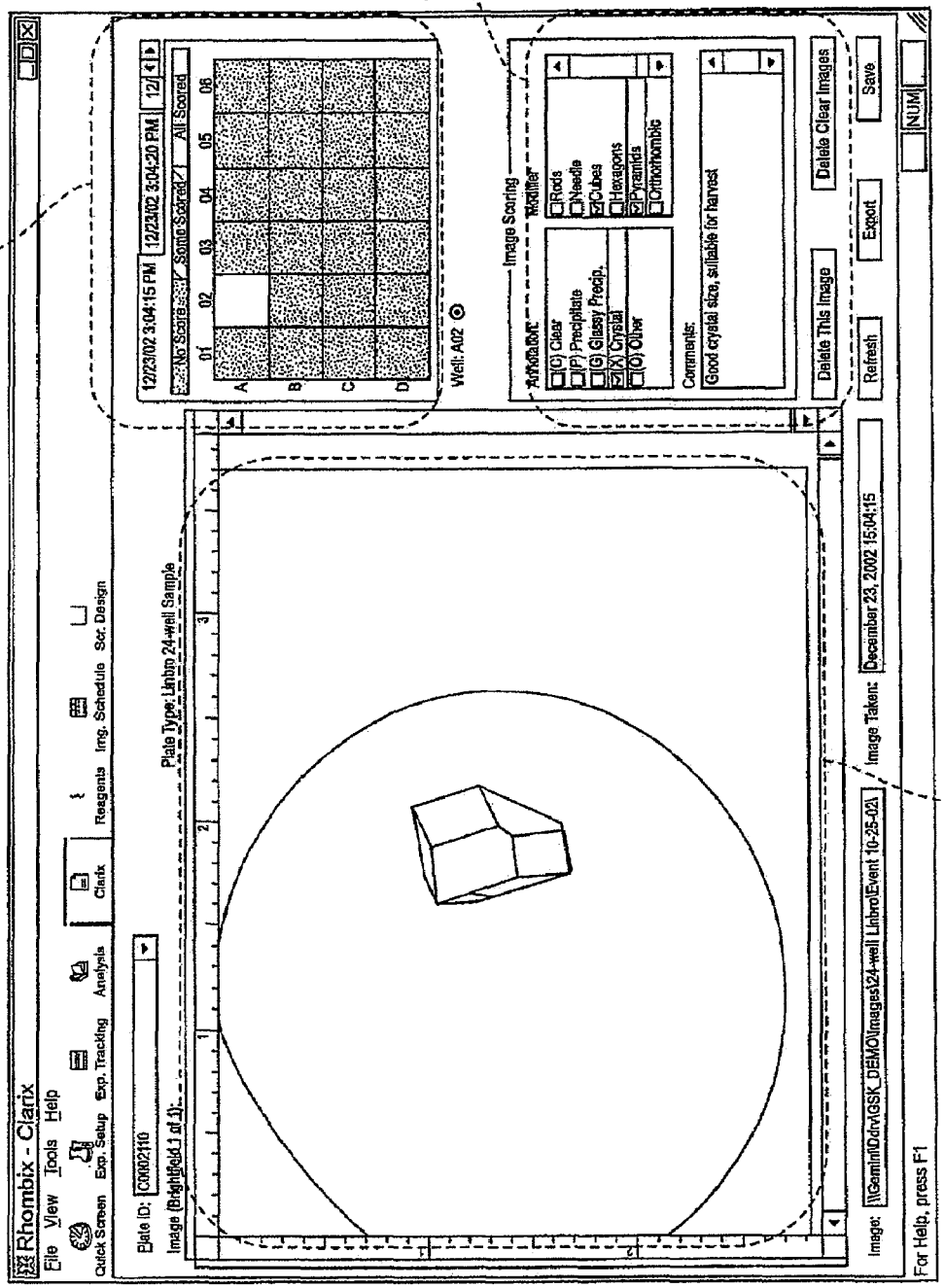
FIG. 25 is a screen shot of a viewing and scoring computer application according to one embodiment of the invention.

In a semi-automatic mode, each plate is associated with an image mask as in the automatic mode, but the operator is allowed to make adjustments to the image acquisition process such as contrast, magnification, focus, light configuration, etc., for each image position. After the plate has been positioned to acquire an image, a real-time image is displayed on the operator's interface as shown in FIG. 25 and the operator may adjust the settings as desired. Once the operator is satisfied with the image settings, the image is captured and the operator then can either acquire additional images of the same well, or may choose to move to the next image location that has been preselected in the mask settings. Once all image sites per the mask have been processed, the plate nest is extended to the load/unload position where the plate is removed.

In the manual mode, the plate is loaded manually, and there is no image mask associated with it. The operator manually selects the desired satellite wells or positions to image and is able to set the same imager configuration settings as those mentioned in the semi-automatic mode. The operator controls plate loading and unloading before and after image processing is performed.

Figure 14:
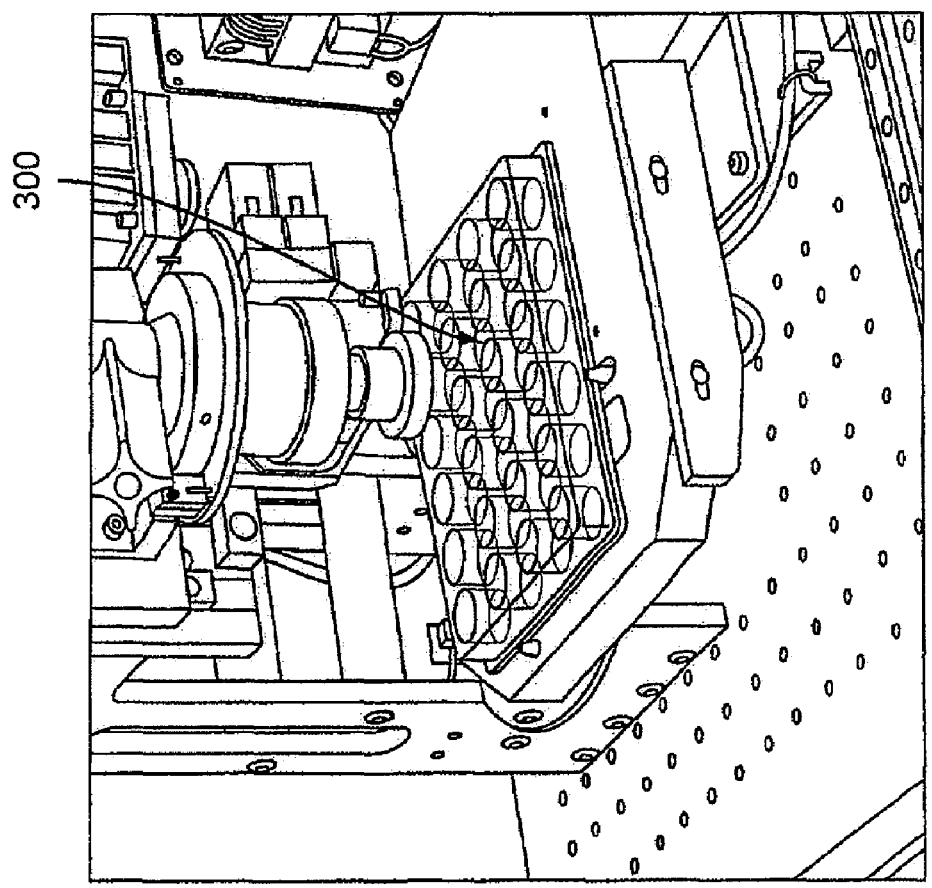
FIGS. 14 and 15 are perspective views showing accommodation of different imaging plate types by the plate nesting holder according to one embodiment of the invention.
Figure 15:
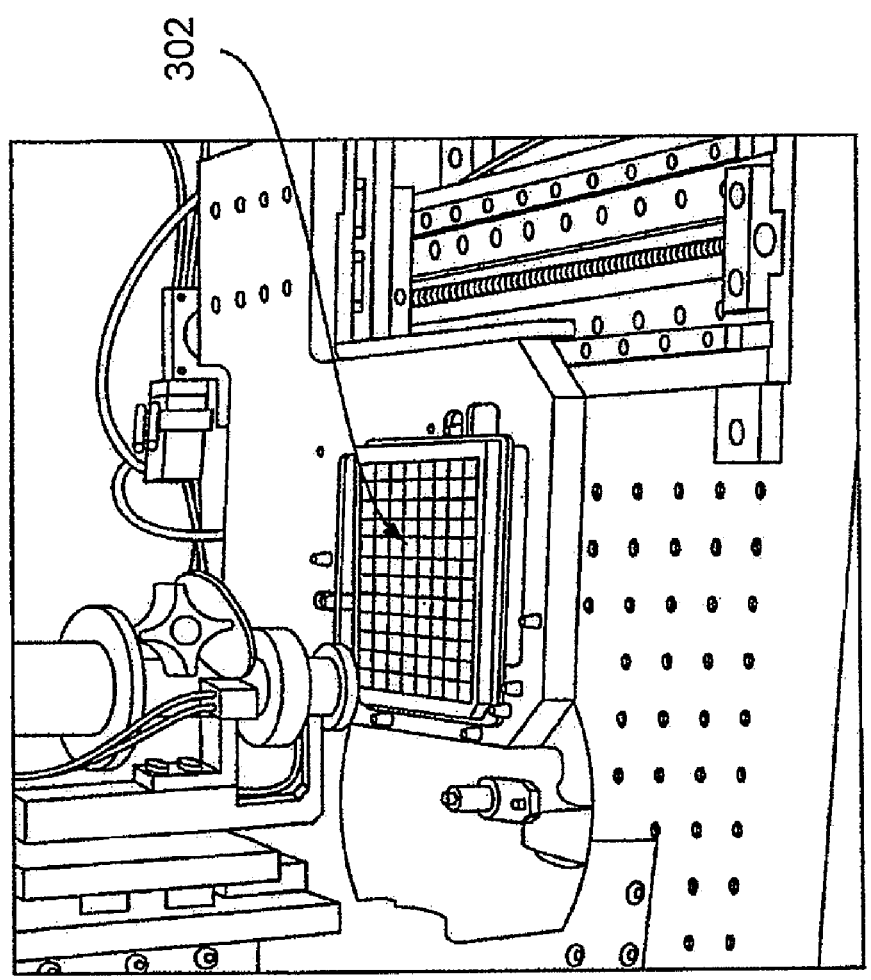

The imager accommodates all presently known protein crystallization plate formats. The imager plate nest supports all SBS (Society for Biomolecular Screening) format plates 302 with heights ranging from the thinnest glass slide capable of supporting drops (approximately 0.1 inch) to 1.6 inches as shown in FIG. 15. The nest also supports large-well Linbro/VDX plate sizes 300 as shown in FIG. 14. As shown in FIG. 14, the linbro plate format 300 is loaded in portrait format.

Figure 16:
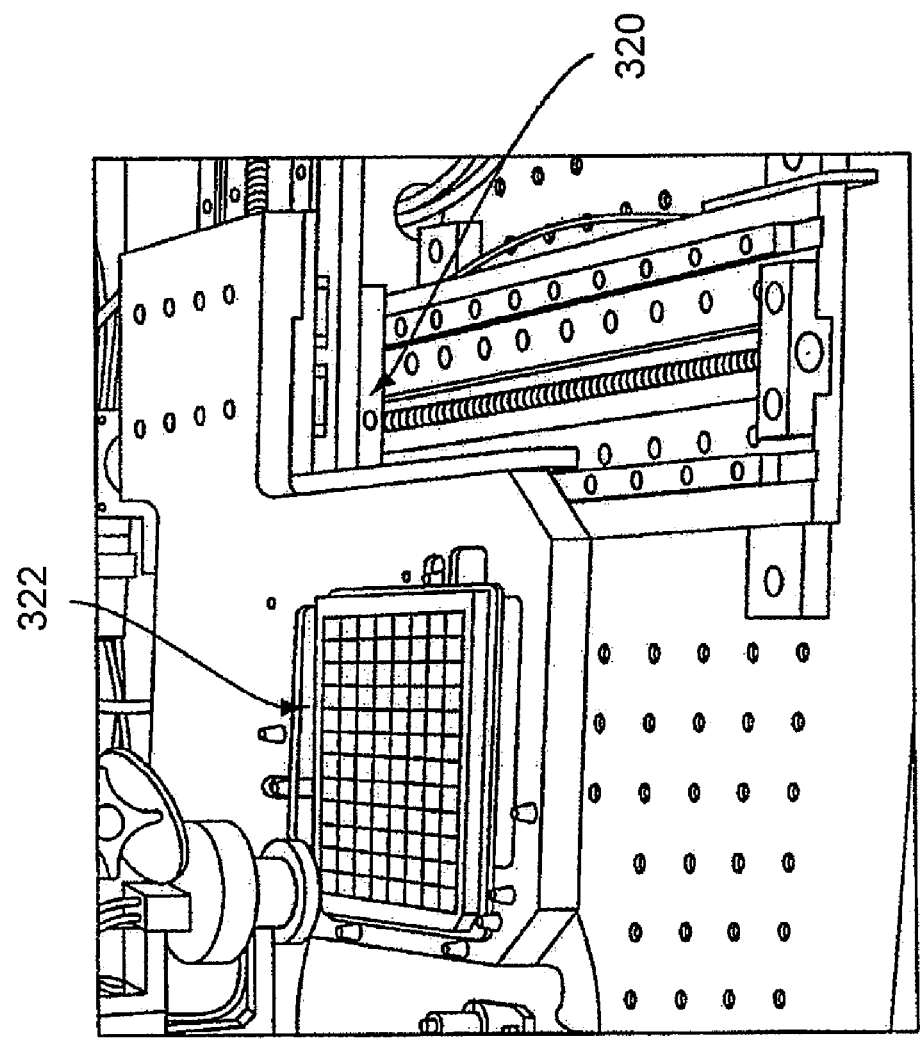
FIG. 16 is a perspective view showing an XY servo stage connected to the plate nest to enable precise well positioning control with respect to the imaging optics.

The imager stage, shown in FIG. 16, is a three axis servo-controlled device (XY Servo Stage 320) which allows motion in the plate horizontal plane (X and Y axes) and in the camera vertical plane (Z axis). Control of each axis is independent of the other axes, allowing an infinite range of positions, which is necessary to accommodate all of the various plate formats that are commercially available. The stage positioning resolution allows the smallest well format to be accurately positioned for imaging. It has been found that by linking the camera auto focus routine to the Z axis via a mathematical algorithm focus compensation during zoom operations is accelerated. In addition to the plate nest 322 stage, the variable transmitting polarizer and the lens focus mechanism also are servo controlled.

Figure 17:
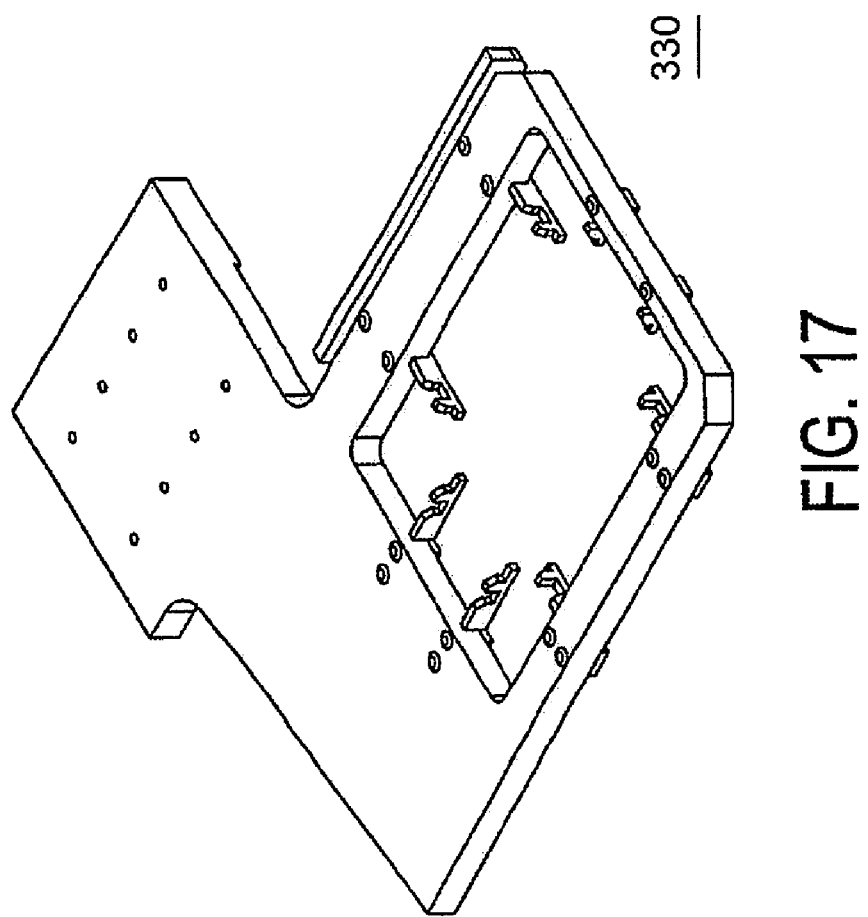
FIG. 17 is a perspective view showing plate accommodation details of a plate nesting holder according to one embodiment of the invention.
Figure 18:
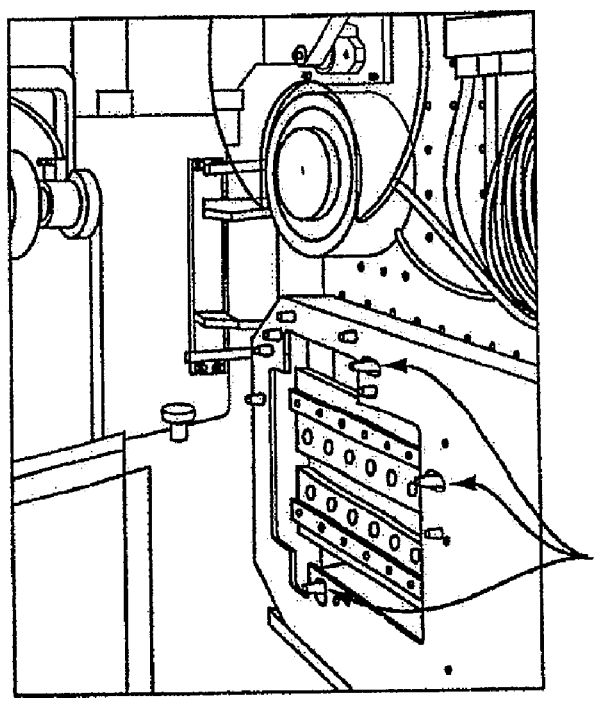
FIG. 18 is a perspective view showing plate centering cams integrated into the plate nesting holder according to one embodiment of the invention.

The imager nest 330 is shown in detail in FIG. 17. The nest is designed to handle SBS and large-well Linbro formatted plates as explained above. As shown, the nest is designed to have a relief to allow the maximum amount of light to pass through the wells located on the edge of the plate. The plates are held in the nest by a number of nest fingers as shown, such that the plates "ride" above the nest platform. It has been found that the relieved nest mitigates shadowing effects on the wells located near the edge of the plate, thereby dramatically improving image quality. FIG. 18 is a perspective view showing plate centering cams 340 integrated into the plate nesting holder according to one embodiment of the invention.

Figure 19:
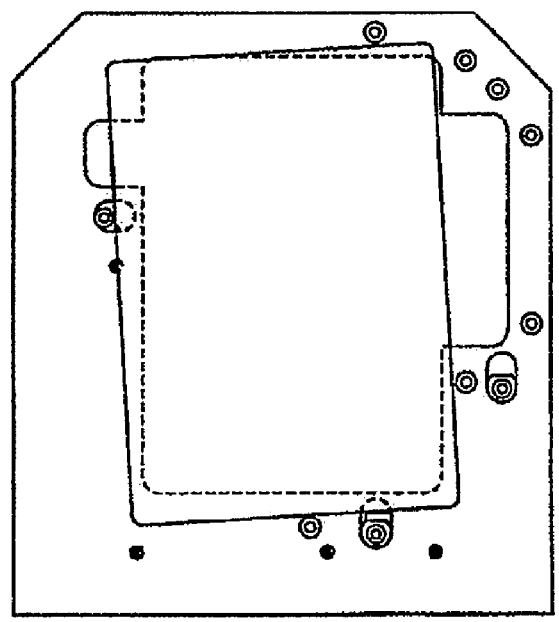
FIGS. 19 and 20 are views showing the operation of the plate centering cams to automatically center a misaligned portrait oriented plate in the nesting holder.
Figure 20:
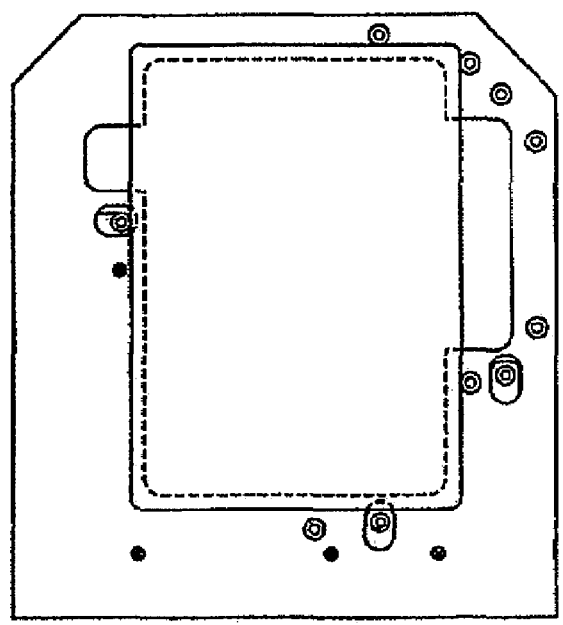
Figure 21:
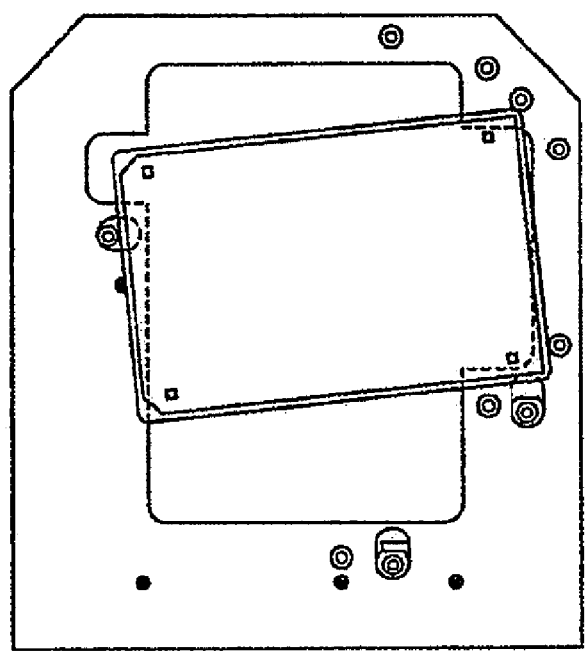
FIGS. 21 and 22 are views showing the operation of the plate centering cams to automatically center a misaligned landscape oriented plate in the nesting holder.
Figure 22:
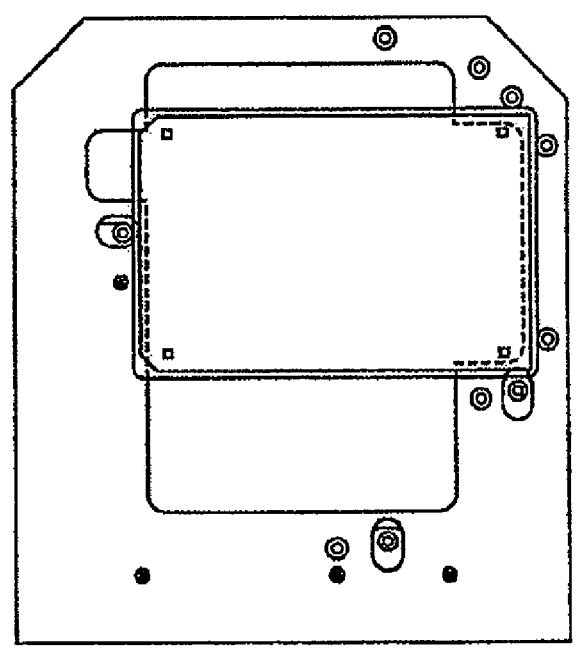

As shown in FIG. 15, the nest includes an active plate orienting system. This system uses a multiple cam mechanism which forces the plate into the correct orientation regardless of plate placement in the nest. As shown in FIGS. 19 and 20, the caroming mechanism automatically centers plates inserted in a portrait orientation, and as shown in FIGS. 21 and 22, the camming mechanism also automatically centers plates inserted into the nest in a landscape orientation. The cam locating pins are opened as the plate nest is extended into the load position and are then closed when the nest is retracted into the main housing of the imager. Correct plate orientation is necessary to provide the required accuracy to locate and image the plate at high magnifications. The active cam mechanism provides an automated methodology to correctly orient all plate types.

In a manual loading mode, the imager nest is fully extended with the cam centering devices open. A plate is placed in the nest either in portrait and landscape fashion depending on the plate type by hand. The operator instructs the imager via the GUI to begin imaging. Once the image operation is completed for that plate the nest is extended so that the plate is presented to the operator as shown in FIG. 8 with the plate centering cams open. The operator removes the plate by hand completing the manual loading and unloading process.

Figure 9:
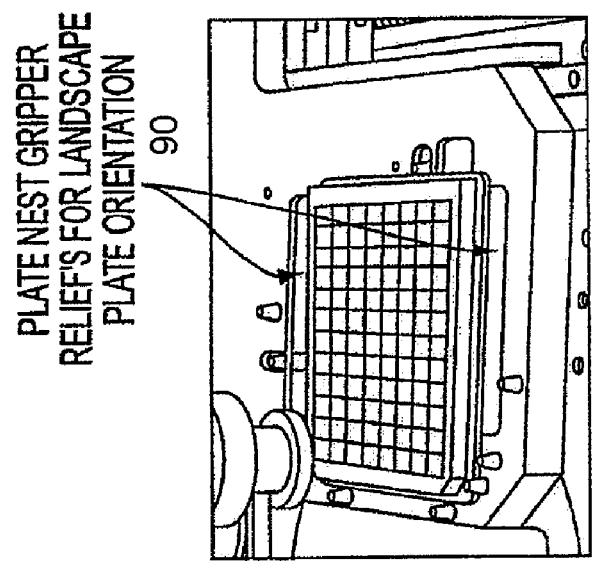
FIG. 9 is a perspective view of the plate nest holder showing cut outs to accommodate a robot plate gripper.

In the automatic and semi-automatic modes, the imager may be loaded via robotics. The nest is commanded to extend via a series of communications from a high level robot controller. Once extended the imager reports back to the controller that it is ready to load and the robot then places the plate in the imager in either portrait or landscape orientation depending on the plate type. As shown in FIG. 9, the nest has cut outs specifically located to allow the robot grippers 90 to move down into the nest while still gripping the plate. The plate is placed in the nest and the grippers are opened. The robot retracts and sends a signal to the imager that it is clear of the nest and that the plate is located in the nest. The imager retracts the nest, which causes the plate centering cams to engage the plate and center the plate. Once the plate imaging operation has been completed, the nest is extended and the imager signals the robot controller that the plate is ready for retrieval. The plate cams are opened as the plate is extended The robot retrieves the plate in the same manner as it loaded it by dropping into the nest along the relieved cut-out portions.

The imager has the ability to acquire multiple high-resolution images of each well position using multiple various well lighting techniques. The multiple image data is then fused to obtain a more complete and accurate understanding of the well contents. Thus, the imager is a true multi-mode device that can analyze a well and determine more information about the well than is possible from a single image event. Specifically the imager can determine crystal presence, clear versus turbid drop contents, micro-crystal field, crystals embedded in a precipitate field, and protein aggregation. Using bright field backlighting crystal detection is enhanced, while dark field lighting enhances precipitate detection, and polarized light can be used to enhance micro-crystal detection. Additionally, due to the properties of the various fluids used in protein crystallization, the drops in sitting well experiments can form a convex or concave shape, which diverts light either away or toward the imaging microscope objective lens, causing undesirable shadowing effects. The dark field light mitigates these shadowing effects by changing the incidence angle of the light on the well. The dark field light will illuminate areas of the well that were not illuminated by the bright field light due to this shadowing effect. Thus the combination of these two lights will mitigate the shadowing effects. The imager also provides for the means to oversize the backlight and thus floods the imaging area with light of various vectors, which has been found to also mitigate this shadowing effect. It has been found that no one single image can fully represent the artifacts of a protein crystallization drop in all cases and therefore a multimode image process is required to produce accurate results in optical protein crystallization analysis.

Figure 10:
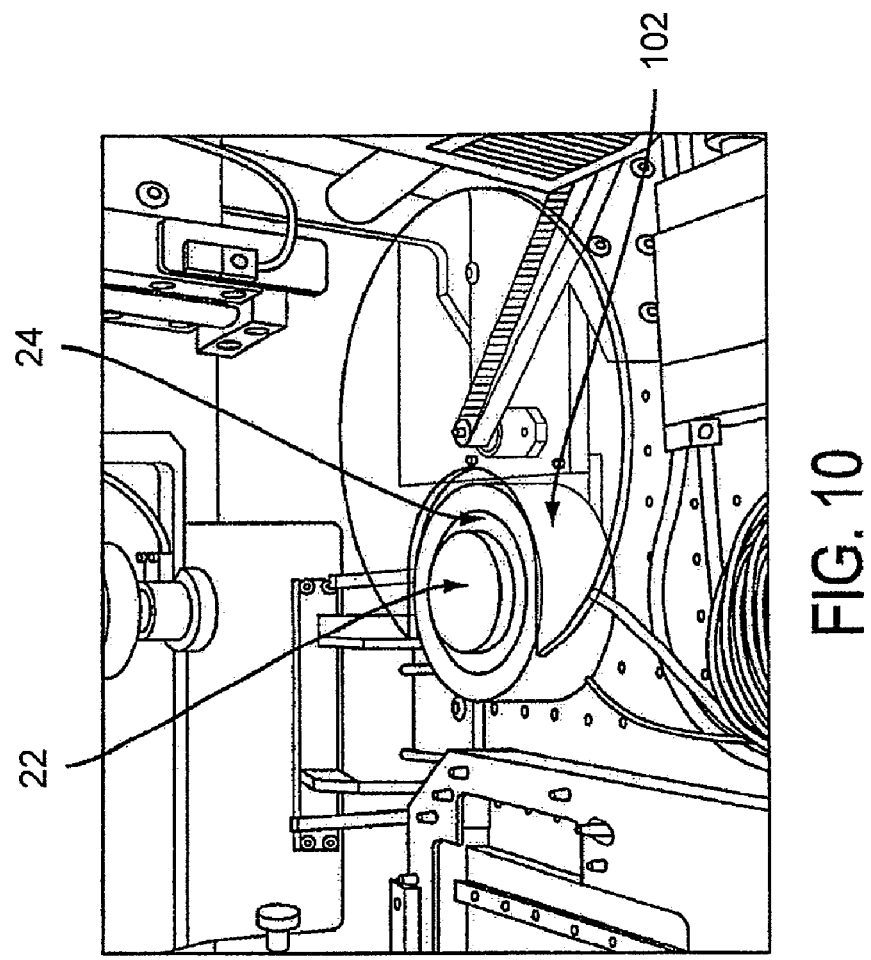
FIG. 10 is a perspective view of the imager light source configurations according to one embodiment of the invention.

As shown in FIG. 10, the imager uses three distinct lighting techniques: bright field illumination (bright field light source 22), dark field illumination (dark field light source 24), and variable angle polarized light illumination (polarizer variable angle transmitter 102). Each light source has a distinct purpose as discussed above. FIG. 10 shows the orientation of each lighting component in the imager. Each lighting technique is controlled separately and can be energized independent of the other sources by a processing controller. This eliminates multiple light effects when collecting multimode data. The imager housing enclosure shown in FIG. 8 provides a light tight environment as well, which eliminates or substantially reduces undesired effects of ambient light entering the imaging plate wells.

Figure 11:
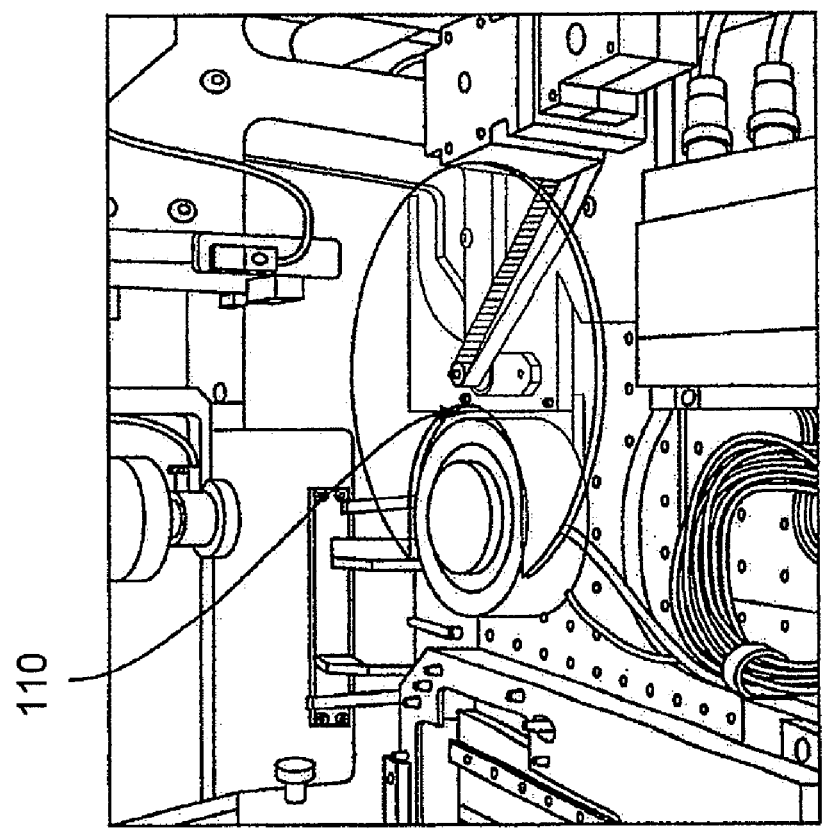
FIGS. 11 and 12 are respective views of a light polarizer filter in a disengaged position and an engaged position.

The bright field illuminating technique is used as a backlight and illuminates the drop using a transmitted light approach. When employing this technique the polarizing filter transmitter is disengaged as shown in FIG. 11 as shown in reference 110, by rotating the polarizing filter so that a notch in the filter aligns with the bright field light source. The light is a special high-intensity low heat generation light. The heat load generated by transmitted and reflected light sources is mitigated through various techniques, including the use of air cooling provided by a fan in the enclosure housing, as well as through the use of heat sink technology incorporated into the light housing, and most importantly by controlling the activation of light sources independently, thereby allowing the light sources to be energized only when acquiring an image. The independent control of the light sources also provides for the ability to vary intensity as well as to energize and de-energize each light source without impacting other light sources in the imager.

The bright field light or back light is built using LUMI-LED technology which offers longer lasting life, has the ability to be energized and de-energized many times without shortening the expected life and burns very cool as compared to a standard halogen source. The LUMI-LED technology offers a great increase in intensity over standard LED technology making the LUMI-LED a significant improvement over standard lighting techniques. It has been found that LUMI-LED technology provides a more stable back light source for protein crystallization imaging with improved control and longer lasting life.

The dark field technique utilizes a standard dark field light source, which has been found to enhance certain aspects of a protein drop image by changing the angle of incidence of the light with respect to the protein crystal drop. The dark field source can be either an LED source with independent control or a standard halogen source using a dark field adapter. The imager provides a means to use either type of lighting.

Figure 2:
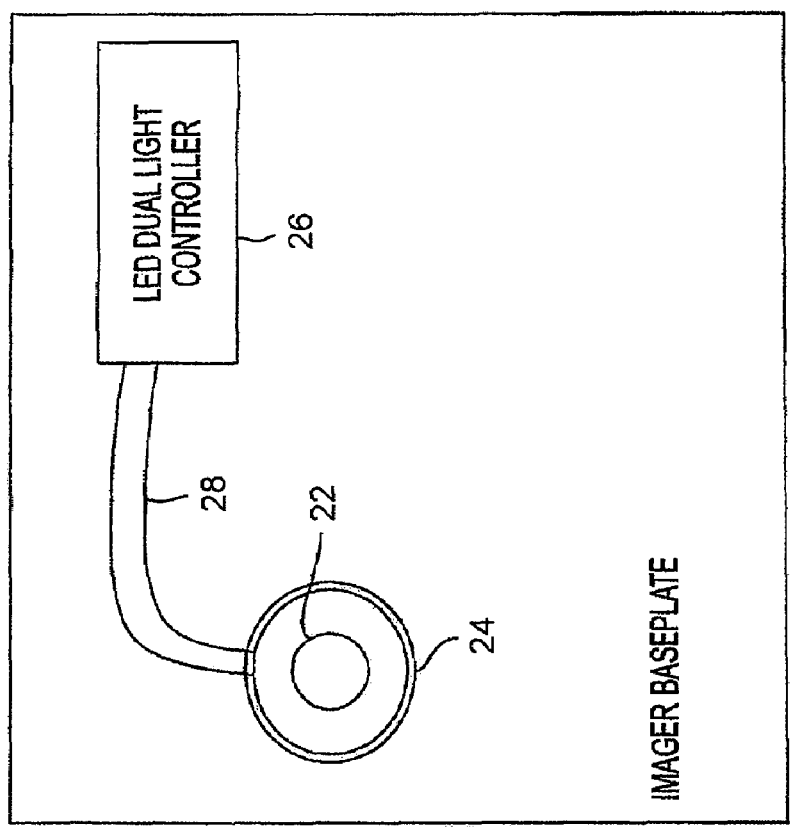
FIG. 2 is a diagram of a combination imaging light source according to one embodiment of the invention using LEDs.

As shown in FIG. 2, the bright field 22 and dark field light sources 24 can be implemented using LED or LUMI-LED technology, and controlled by a dual-light controller 26 via LED control cables 28. The LED dark field source provides a stable long life illumination source for protein crystallization with the added benefit of being able to independently control the light (e.g. vary intensity, energize and de-energize the source without effecting other light sources). This allows the dark-field light to be de-energized during back light operations and energized for dark field operations exclusively (i.e., the bright field light is not energized). This arrangement allows for a clear and distinct light combination to be used in the multi-mode approach prescribed by the imager, which is advantageous in producing higher quality protein crystal drop images.

Figure 3:
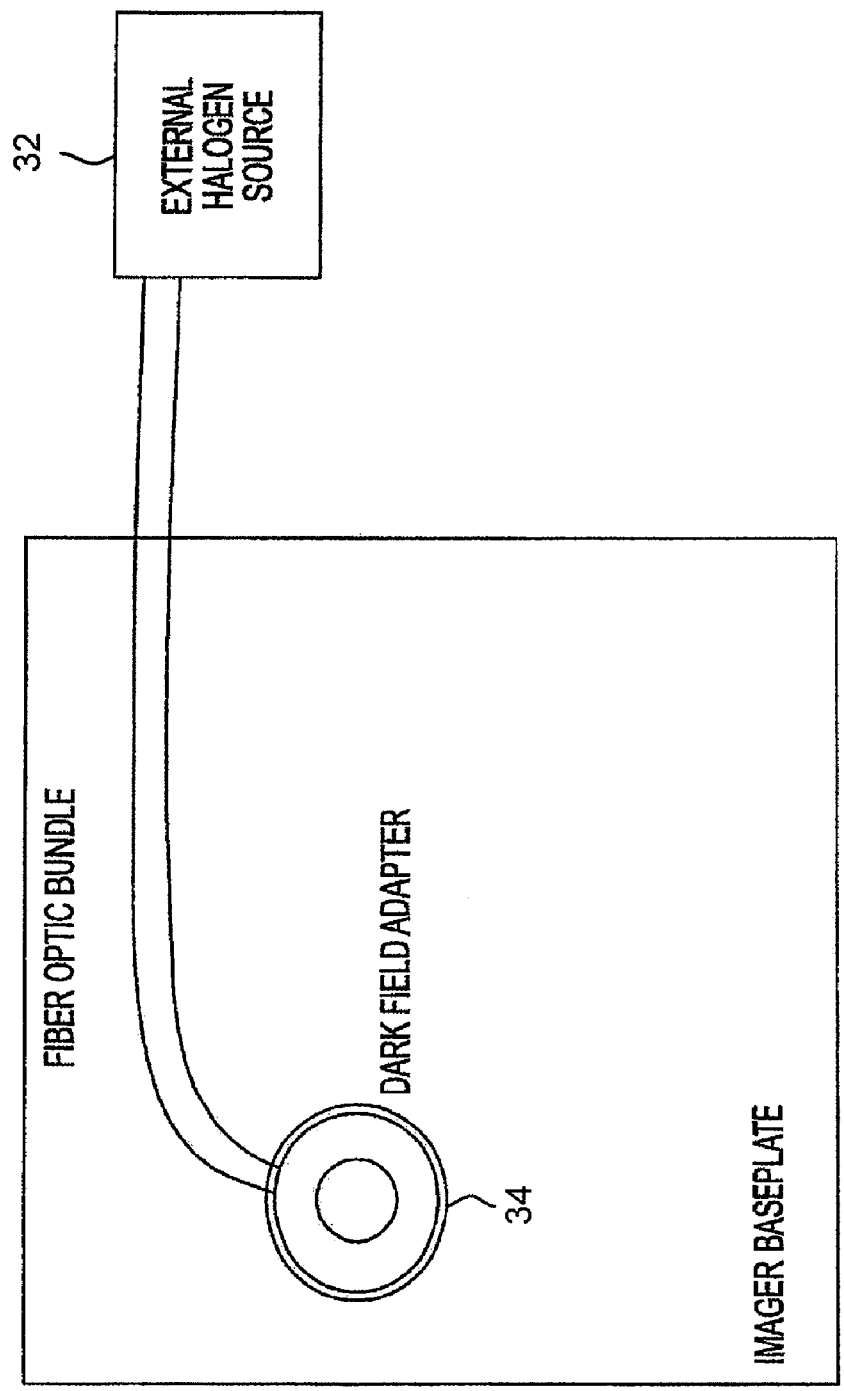
FIG. 3 is a diagram of a combination imaging light source according to another embodiment of the invention using an external halogen light source.

Alternatively, as shown in FIG. 3 an external halogen light source 32 can be used in concert with a fiber optic dark field adapter 34. The benefit of this combination is the generation of very uniform and intense dark field illumination without the addition of the halogen light heat source internal to the imaging enclosure and the resulting negative impact to the protein crystallization experiment, which requires a very uniform environment during the storage and time-lapsed imaging process. The external halogen light source may remain on during all operational modes, including bright field and polarized light illumination.

In protein crystallography polarized light in concert with transmitted white light and a color camera can provide details that are not always discernable to the human eye even with the aide of magnification. Because a property of most protein crystals is bi-refringence, polarized light can be used to find crystals that are either to small to be distinguished by normal processing methods or crystals that may have become occluded in a precipitate field. As shown in FIG. 4 and also in FIGS. 11 and 12, a rotating transmitter polarizing filter 44 is provided between the light source 42 and the imaging plate 46, and an analyzer polarizing filter 48 is placed between the imaging plate 46 and the imaging optics.

The physics of light travel is such that if a polarizer transmitter and analyzer are set to extinction angles that no light will pass; therefore, it has been found that if a protein crystal is not perfectly aligned with either the transmitter or analyzer axes then the light rays will be redirected by the presence of a protein crystal so that light will pass to the imaging optics with the analyzer and transmitter set at extinction, provided that the well is not bi-refringent. In this condition only crystals will be seen; however because many protein crystal plates are composed of materials that during formation also exhibit bi-refringent properties a clean image is not returned during imaging with the analyzer and transmitter at extinction. Instead the plate itself will redirect the light as it passes through the plate by changing the angle of the light to a myriad of axes other than that of the transmitter. The result is a distinct diffuse light signature at the analyzer. In order to mitigate these plate effects, it has been found that by varying the transmitter polarizing angles by rotation of the filter and acquiring multiple images at these various angles and then by transforming the negative of the image and performing image subtraction on the resulting set of images, the polarized composite result displays a higher level of crystal confidence and shape than is possible with a fixed polarizer transmitter/analyzer angle. The orientation of the filters with respect to the object under inspection is critical and must be set so that the transmitter is on the light source side of the plate and the analyzer is on the objective or camera side of the plate as depicted in FIG. 4 and also shown in FIG. 13.

Figure 12:
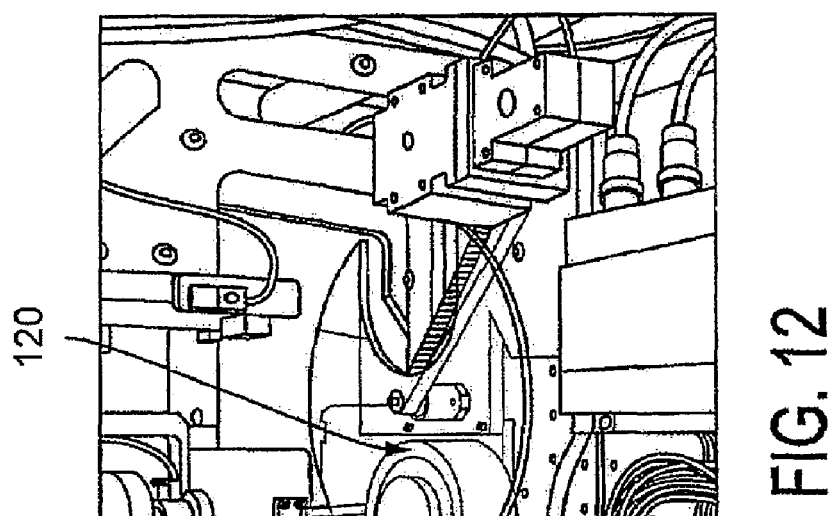

In order to completely filter out light, a technique of employing two polarizers set at 90 degrees with respect to each other is used. This first polarizer filter passes light in only one direction or axis with respect to the angle of the polarizer, this filter is referred to as the transmitter. Therefore with the imager setup shown in FIG. 12, when the transmitter filter is engaged (i.e. inserted between the light source and the imaging plate) as shown in reference 120, light is passed in one axis. This light passes through the crystal plate and then travels to the microscope objective. Prior to entering the objective the light passes through the analyzer polarizing filter, which in the case of the imager doubles as a color filter. In order to accommodate the requirement of variable position based on user desires the transmitter is attached to a servomotor via a non-slip belt and pulley assembly. This arrangement provides complete positional control of the transmitter angle with respect to the protein drop to be imaged. The filter is built by laser etching it into an optically transparent disk and then notching out a portion of the disk so that it can be disengaged when bright field and dark field imaging are desired, as shown in FIGS. 11 and 12. The position-controlled transmitter polarizing filter enhances image processing and data collection in protein crystallization drop analysis.

Figure 13:
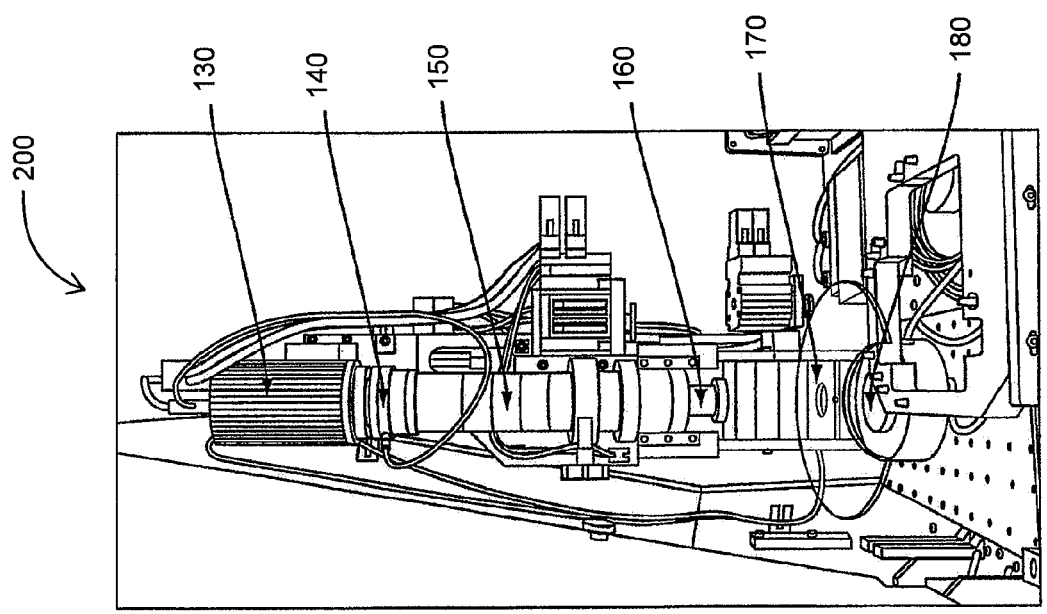
FIG. 13 is a perspective view of the imaging optics components according to one embodiment of the invention.

As described above, a complete polarizing solution requires a transmitter polarizer (or polarizer transmitter) 170 and an analyzer polarizer (or polarizer analyzer) 140. The imager accomplishes this by utilizing the polarizing filter aspect of a color filter 140, which is located between the microscope objective (optics) 150 and the camera 130 as shown in FIG. 13. It has been found that an LCD color filter has the correct optical characteristics to act as an analyzing polarizer filter for protein crystallization imaging. In addition to functioning as the analyzer filter of the polarizing system, the color filter provides the capability to acquire true color images without requiring a multiple CCD (charge-coupled device) camera. The color filter allows three images to be taken with a single CCD array digital camera 130 as shown in FIG. 13, and then combined to form a composite true color image. While other single CCD color cameras without the use of a color filter employ a mosaic approach known as the Bayer Pattern to simulate a color image, the Bayer Pattern does not accurately define a true color image because of the redundant green pixel pattern used.

Turbidity Analysis

The imager supports the ability to conduct light scattering analysis to calculate turbidity of the protein crystallization drop. The is achieved by measuring the amount of light collected over an extended time frame and then filtering the data set to determine light scattering patterns. It has been found that early stages, prior to crystal formation of protein aggregation can be detected using this methodology. The analysis can be conducted using a variety of standard algorithms such as Discrete Fourier Transform, Fast Fourier Transform, Neural Net Filter, and Statistical Filters (such as LQE, LQR, LMS, etc.).

The turbidity detection methodology uses a light scattering or collection technique to determine a turbidity measure of the well. The imager can utilize different approaches to conducting this methodology. Two such methods are described below for completeness; however, by changing the light source and collection device the imager can support other approaches to turbidity analysis.

According to one embodiment, the imager can utilize a laser, which is tuned to the appropriate wavelength and mimics the approximate size of the object under analysis (in the case of the imager, a protein crystal drop). The laser beam is transmitted through the drop and a collector on the opposing side of the drop measures the transmitted light level. The more turbid the drop, the greater the resulting light attenuation. This measurement is taken over a period of time and is coupled with the image data in order to show in clear to semi-clear drops early stages of protein aggregation as previously explained. The laser light passed through the crystal plate well is measured for intensity over a period of time so that any deviation can be mapped over the sampling period and correlated with corresponding image data in order to detect early stages of protein aggregation.

The imager also can employ the ability of a digital camera to measure light intensity while employing bright field, dark field, or laser lighting techniques. The premise is identical to that stated above using a laser emitter collector approach. Thus, according to an alternate embodiment, the light intensity focused through a well can be measured over a period of time using the CCD array of the digital camera to capture the light intensity variations.

As shown in FIG. 13, the imager 200 uses a true microscope objective 150 to enhance image depth of field (DOF) and provide the ability to focus through a very large range of field of views (FOV). The result of this type of optics provides a large range of magnifications that can be used by the imager. The imager 200 also includes light sources 180. It has been found that this approach allows for more dynamic range of FOV, DOF and magnification than a standard set of optics with a variable magnification lens.

The imager employs a digital camera to capture a high resolution image and to allow digital image processing to occur. The camera employs a high speed data transfer ability to move the data from the camera to the associated user computer (not shown). The camera has the capability to merge three single color images of the same object into one composite true color image.

The camera produces images which can vary in resolution dependent on user desires. The higher the resolution of the image, the increased likelihood of small object detection; however, the image data size also increases with resolution. It has been found that lossy compressed data images can be manually scored, but a lossless compression is required for automatic scoring accuracy. Therefore, according to a preferred embodiment, the imager saves a lossy version of the image for rapid manual scoring and a lossless version for automated scoring in various image formats which are user selectable.

The imager has the ability to acquire full color or monochrome images at a high resolution. The imager allows the operator to select the mode and resolution of the images to be taken in semi-auto mode or ahead of time for the entire image set run in auto mode.

Figure 23:
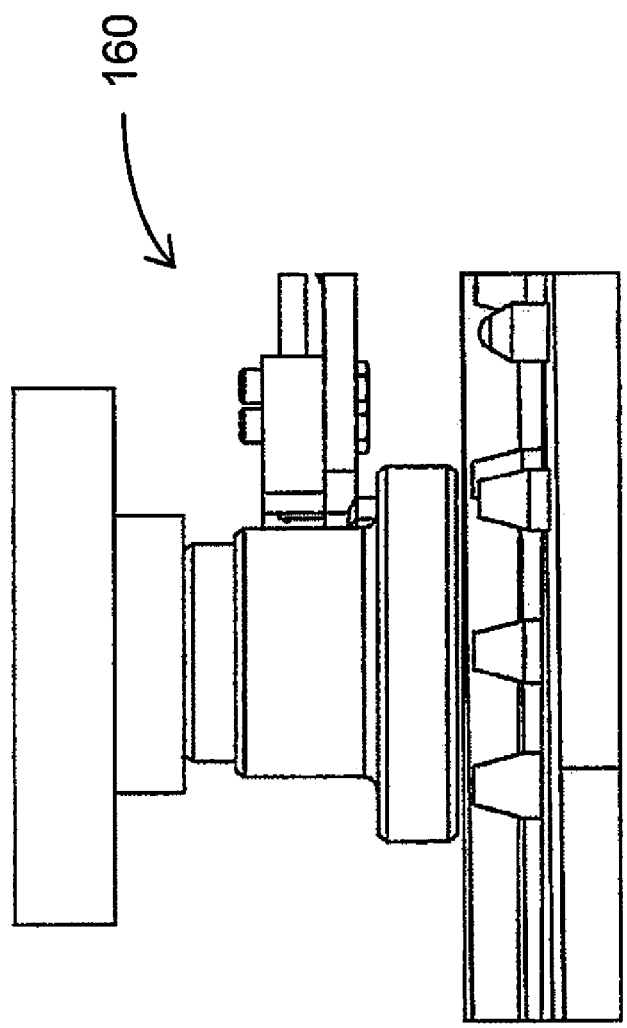
FIGS. 23 and 24 are views showing the operation of a Z-axis pressure sensor to detect pressure exerted on an imaging plate as it is engaged with the imaging optics, to prevent damage to the imaging plate.
Figure 24:
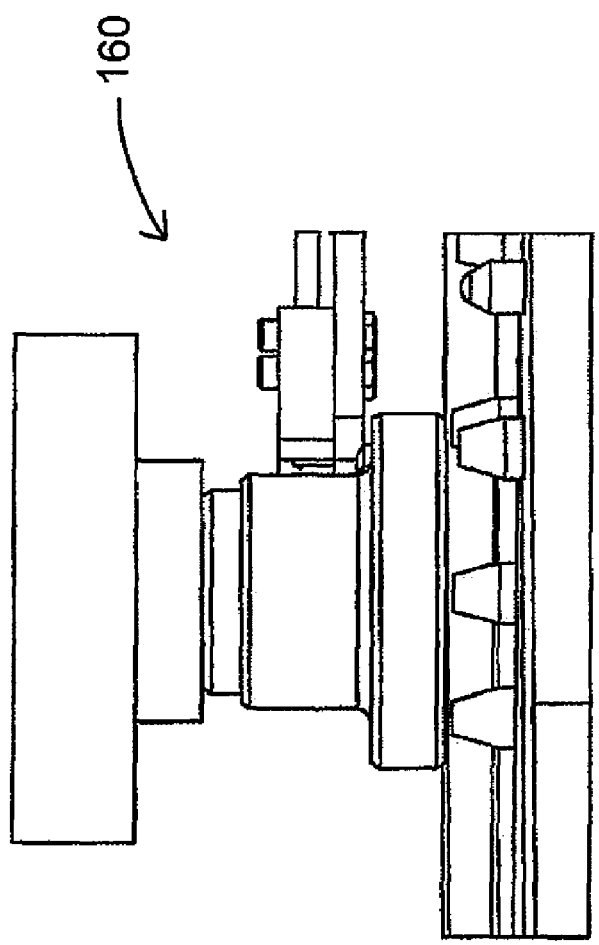

In FIG. 13 a Z Axis pressure sensor 160 is shown mounted at the end of the microscope objective (optics) 150. This sensor 160 is used to detect the presence of the top of a plate contained in the nest without applying a force to the plate. The sensor has a compliant ring that rests below the horizontal plane of the microscope objective (lens) as shown in FIG. 23. As the sensor comes in contact with a plate as shown in FIG. 21, the sensor ring is pushed upward. As the sensor is displaced, a focused beam of light to a optical detector that produces a signal when the light beam is obstructed. This detector sends a digital signal to the imager servo control system indicating an anomaly in the Z position of the lens. The z-axis servo travel in the positive or down direction is then blocked to avoid a crash scenario, thus protecting the plate and the objective.

The imager also utilizes a vibration damped baseplate that is constructed using a honeycomb composite. This plate design is lighter than Granite damping plates and affords a ready methodology to mount the imager components to the baseplate without requiring special purpose tools and fasteners. The vibration damped baseplate provides real time platform stability isolating stage movement during image acquisition of protein crystallization plates and therefore mitigates settling periods required for image capture after plate movement is complete.

Software Components

The imager utilizes a sophisticated set of software components to control, acquire, and analyze the protein crystallization imaging process. The imager control system reads specific instruction sets for each plate via a database (not shown). The instructions are associated with the plate barcode so that each plate has a macro associated with the experiment analysis set to be run for that particular plate. This methodology allows for unique experimental analysis steps to be followed on each plate independent of other plates in the system at that or any previous time. The following is an explanation of the various software modules that are utilized in the imager.

The imager acquires images digitally and transfers the images from the camera via a high speed data transfer medium such as IEEE 1394, Fast SCSI, or a camera proprietary portal to an image processing PC. The images are associated with the plate barcode and well identification code (e.g. A1) in the database by having the control system identify the plate barcode either robotically or manually depending on the operation and then associating the well ID from the servo positioning software with the acquired image or multiple images of each well. All of this information is saved together with the actual image location in the database. The imager uses an image mask to acquire the designated images for a particular plate as described previously, which image mask also is stored in the database. The camera is triggered to acquire the image from the imager control system software once the plate is correctly positioned under the lens, which information is fed back to the controller from the servo positioning algorithms (which are well known and therefore will not be further described herein). The images are either concatenated in the digital camera before being transmitted to the control system computer or are sent to the controller and are processed and merged into a high resolution composite image at that point. The image processing and system control algorithms used by the imager are described below.

Figure 5A:
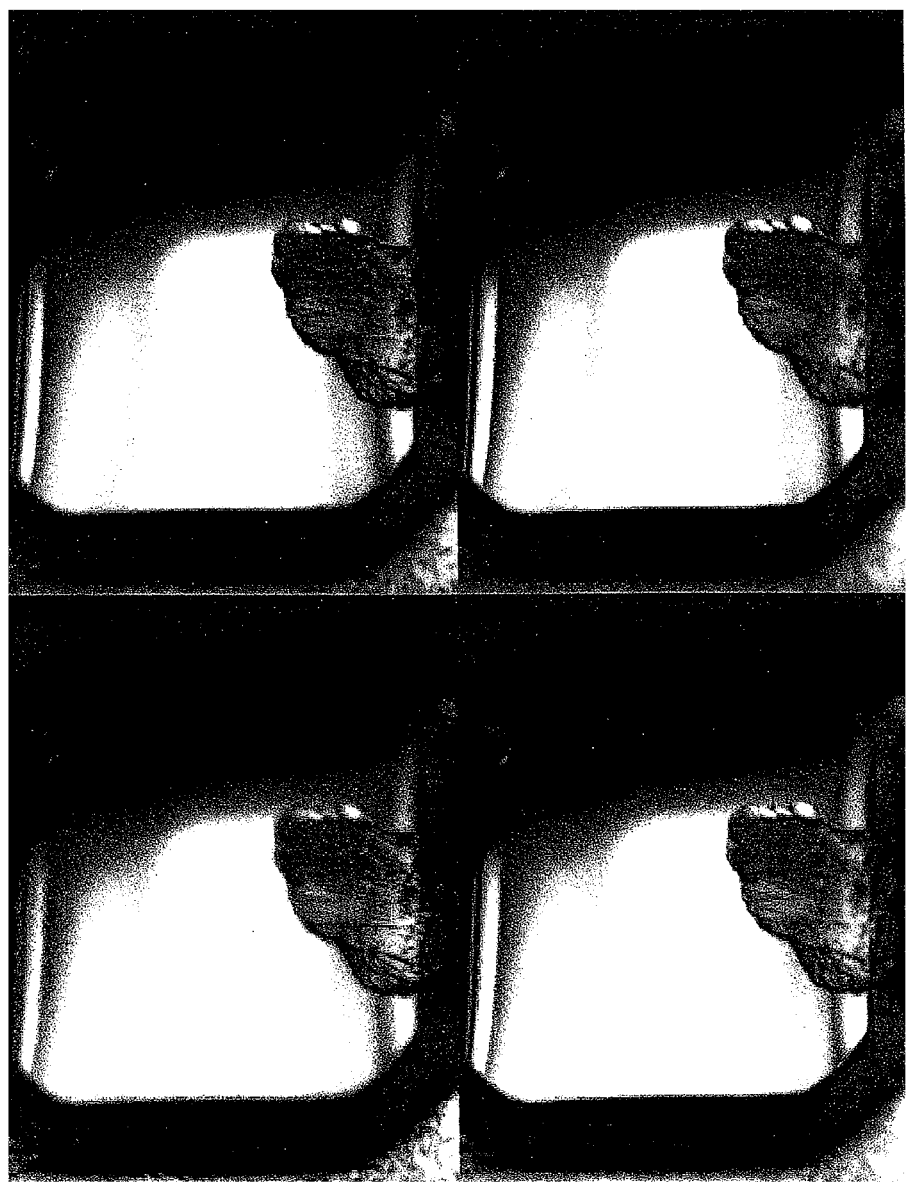
FIG. 5a shows a series of narrow focus images of a protein crystal taken at different focus depths.
Figure 5B:
FIG. 5b shows a composite extended focus image obtained by combining the narrow focus images of FIG. 5a, according to another aspect of the invention.

The imager has the ability to automatically merge multiple images of narrow depth of field as shown in FIG. 5A, into a single extended focus image as shown in FIG. 5B. In this example four images of a protein drop with crystal growth are merged into one extended focused image. The process to create the merged image requires four steps, which are described in FIG. 6. As each image 62 is acquired, a median filter 64 is applied to a copy of the image 62 to remove any noise in the image 62. The median-filtered image is then processed with a two dimensional edge detector (Sobel detector) 66 to create an edge image that is placed in a local maximum map 68. After all desired images have been acquired and processed, each edge image is searched on a pixel-by-pixel basis within a variable neighborhood to determine which image has the greatest edge value. The image with the greatest edge value then contributes its original image pixel to the final merged image 70. The final merged image 70 is then constructed pixel-by-pixel using the process described above.

The imager also has the ability to automatically focus the image currently in the view. This is a two step process. When the user actuates the auto focus capability the imager begins a search routine using standard deviation of the image as a measure. A second order curve fit is used to predict the position corresponding to the maximum standard deviation of the image. A second search is performed using a smaller range and step size and using a Tenengrad measure in place of the standard deviation. The maximum Tenengrad value is used as the focused position. In addition the auto focus routine can use a region of interest to determine the optimum focused position allowing the user to focus on a specific region of the image.

The imager further has the ability to automatically find the optimum exposure for the image. The camera has an integral capability to rapidly sample a range of exposure levels and select the value for the image with the lowest saturation level. By default auto exposure works with the entire image but a region of interest can be specified. The imager also has the ability to automatically set the white balance for the image.

The camera has an integral capability to sample a user selected pixel in the image and adjust the individual color balance to force that pixel to be white.

To determine whether polarization is to be used the imager control system software reads the database using the plate barcode and determines the necessary experiment setting to analyze the plate. Once the plate is loaded in the imager the polarizer is positioned to the desired angle and an image is acquired. Multiple images at various polarizer angles can be taken if the user has requested this in the experiment setup. Each polarized image is saved and associated with a single image event for the plate and the well in the database. These images can be used to provide a more comprehensive view of the well contents based on the various polarization effects. As discussed previously most protein plates have a bi-refringent property and therefore multiple polarization angles can provide more data to enhance accuracy.

The imager can save images in any format where a defined codec is available under the Windows Operating System. Such known codecs include JPG, BMP, PNG, and TIF. Any other image encoding formats that provide similar quality and capability also can be used according to the invention. The imager may use uncompressed BMP format against which to conduct automated scoring (image processing) techniques. The user selects the format to be used for images to be saved for manual viewing. These formats may employ an image compression algorithm that will greatly accelerate the annotation and manual viewing process.

For turbidity analysis, the imager associates the results with the plates and well positions in the database. The time lapsed results for a single well are then passed through a filter which estimates and predicts light scattering or absorption by the well and its contents. The algorithm takes the data points for a well for each image event and passes the values into a statistical filter to calculate the deviation of the measured light intensity over the course of the recorded image events. In addition the values are statistical predicted for future events as well as predicted using a neural net estimator. These values are used to predict early stages of protein aggregation.

The data related to a particular well on an imaging plate is stored in the database, and the stored data then is collated or fused by an engine which performs a series of statistical and rule-based processes to more accurately discern well contents and predict future well conditions. These results become the final score associated to the well in the database while all of the original well data is still maintained. By fusing the data sets associated with a well and applying basic statistical methods, adaptive filtering techniques and custom rule-based processes, a more accurate assessment of the well contents can be made.

The imager can use image processing algorithms to automatically find crystals and precipitate in well images. These algorithms coupled with the various images taken in the various different modes can be used to more accurately characterize the well contents for protein crystallization. The image processing algorithms utilize "blob" finding techniques, morphological techniques, edge, and centroid detection techniques to fully qualify the well contents from a digital image processing approach. By using standard advanced image processing software algorithms clear drop discernment, precipitate recognition, and crystal recognition can be achieved. Furthermore early stages of protein aggregation can be modeled and identified using advanced statistical methods such as digital filter and adaptive filter methods. Such statistical and filtering algorithms are well known in the art and therefore will not be further described herein.

The imager supports manual annotation and viewing of the images taken by the system in one of two modes: offline post-image acquisition and online real-time annotation during the acquisition cycle. FIG. 25 depicts one of the interfaces 400 supported by the manual image annotation software. In this FIG. 25, the image viewing area 402 allows a detailed look at the complete image as well as the ability to zoom to a region of interest either digitally (post image acquisition) or zoom and acquire a new image (real-time during the image acquisition process). The viewing window also supports measurement tools that are associated with rulers that encompass the viewing window or by defining a region of interest on the screen via a pointing device such as a mouse, using standard practices adhering to the Windows Operating System Style Guide. The imaging area can also be changed to view multiple images at one time in a thumbnail format. These images can be either time lapse views of a single well on a particular plate or images from a common plate that were taken during a single image event (i.e., at the same relative time). The location of each image in its perspective well is shown in the plate map 404. Furthermore the plate map 404 also shows all of the previous image events for a particular plate across the top of the plate map in the form of a tabs which show the date and time of the image event. The previous image events can be viewed in detail mode by selecting the desired tab on this interface. The images can also be annotated via this interface in either offline or online modes. The annotation field 406 shown in FIG. 25 is user configurable and is established from the database to which the users have access in order to modify via another application. The annotation names and modifiers can therefore be customized by each user. The user can select the desired annotation and modifier to associate with a particular image, and also has the option to describe the image in a narrative format. The resulting annotations are associated with the image in the database via the plate barcode and well location fields.

Figure 7:
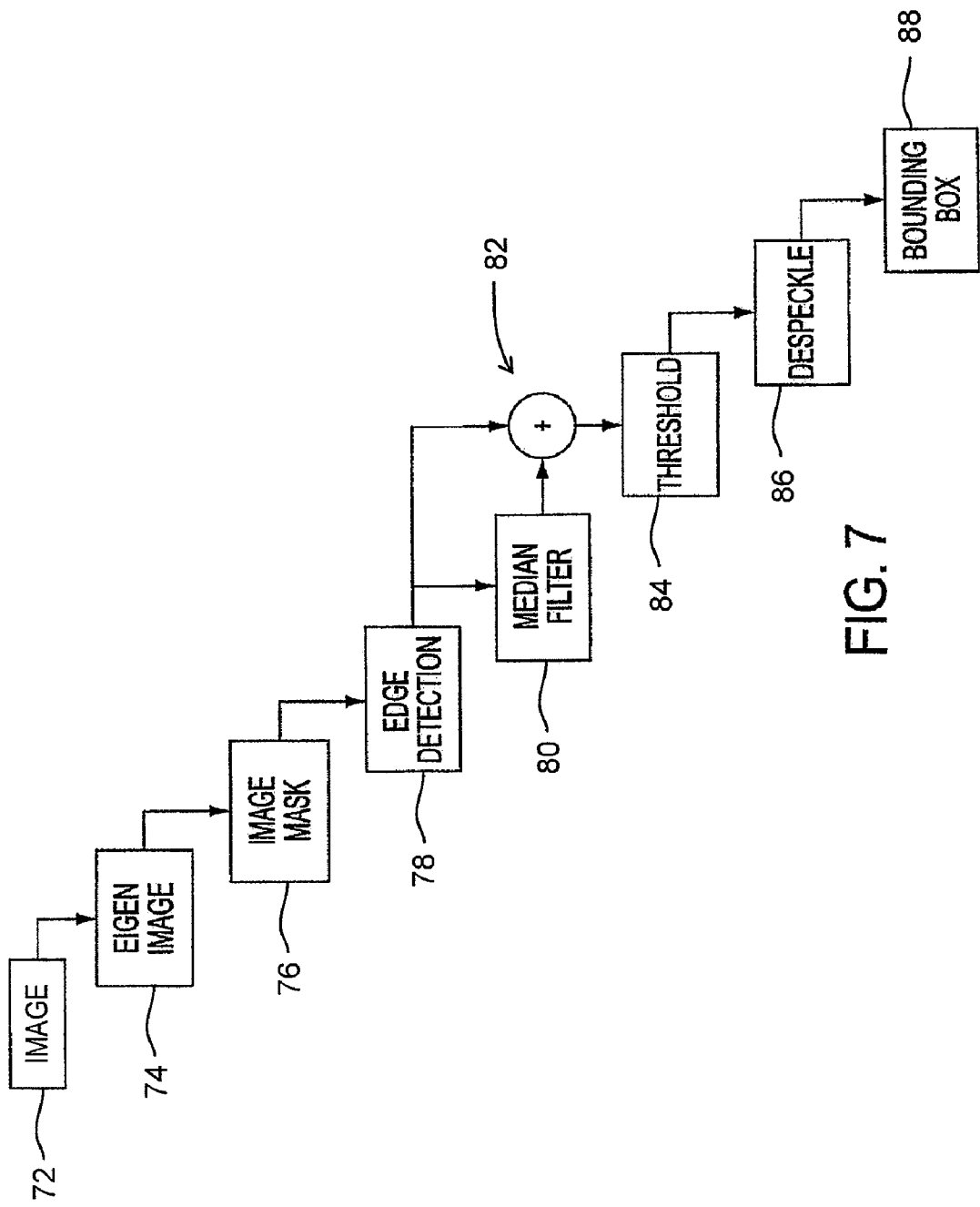
FIG. 7 is a flow diagram of one embodiment of a process for detection of protein drops on a "hanging drop" plate according to the present invention.

The imager also supports the use of an automated scoring routine which utilizes adjective annotation parameters defined in the database and associates a numerical score to the appropriate adjective annotation. The scoring routine first assigns a set of numerical values to the fused data component of the image in question. These values are then related or mapped back to the adjective scoring system customized by the user. The adjective scoring system consists of a noun description and an adjective modifier (e.g., crystal/needles), which are related back to the numerical score by a map maintained in the database. Thus the automated scoring system can return numerical scores as well as associated adjective scores. The imager has the ability automatically find drops on hanging drop-type plates. When a hanging drop image is acquired, the steps shown in FIG. 7 are performed to determine the bounding box of a drop. This allows the imager automation to zoom in and maximize the size of the drop in the image. In particular, after an image 72 is acquired, an Eigen process is performed on it to generate an eigen image 74. The eigen image is masked 76 and edge-detected 78. The edge image is filtered through a median filter 80 to remove noise and the filtered image is compared 82 with the edge image to determine a boundary of a drop in accordance with a predetermined threshold 84. The image in the determined boundary is then despeckled 86 to form a bounding box drop image 88.

The imager database allows the tracking of all interactions of the imager with crystal plates. The first time a plate type is loaded into the imager by a user, the user will define it for subsequent use by other plates of similar construction. Physical geometry information such as number of wells along each axis, well pitch of each axis, number of satellite positions, offsets to satellite positions, plate height, and plate style (Linbro/SBS) is stored in the database. In addition, certain camera settings related to exposure, gain, focus, and polarization are associated with each satellite well defined on the plate type and stored in the database.

Once plate types are defined, the system can accept any plates of that plate type for imaging. Plates are identified by a unique label or barcode in the database. After loading and either scanning or entering a plate label or barcode, the imager will look up the plate in the database. If it exists, it will load the plate type information that this plate is based on. Entry of new plates will cause the imager to prompt the user to select an existing plate type or define a new plate type. After the plate is associated with an existing plate type, the user can begin imaging it. Each time that a user initiates the imaging process, a new image event record is created in the system. Image events group images of satellite positions on plates by the date they were acquired. The database records the path to the satellite position, image event, image file path on disk, millimeters/pixel, polarization angle, image type (Bright Field, Dark Field, or Polarized), and image formats (JPG, BMP, PNG, TIF). Multiple images of the same or differing types may be acquired for a particular satellite during the same image event. Once image acquisition is complete, the resulting images may be annotated with notes or scored via a set of descriptors and modifiers that each customer defines. Annotations occur on a per image event satellite position basis-taking all images acquired during that event on that satellite position into account. The database allows multiple descriptors and modifiers to be selected for each annotation. In addition, multiple scoring methods are supported (manual, automatic, light scatter) by the database.

The user has the option to store either all images, non-clear images, images with crystal detection hits or any combination thereof. The settings for image storage are stored in the database and can be filtered by the user to obtain the desired results for that particular user. The images themselves are not stored in the database, but rather only the image locations. This allows the database size to remain small and manageable while still providing a link to the image via a single interface for future reference and possible scoring. The images for a plate for a particular event are located in the same directory that is named for the image event. The file path is recorded and maintained in the database. It has been found that maintaining the images external to the protein crystallization database allows the database size to be managed to a smaller size increasing efficiency of search and query algorithms.

The imager also supports an automated plate scheduling algorithm. The plate schedules are associated with the plate barcode in the database. The imager scans the database to register the next plate scheduled to run in the imager. The plate schedules can be superceded by manually introducing a new plate to image at which time the plate scheduled to run will be delayed and run after the manual plate is completed. The scheduling algorithm also supports multiple resource management when more than one imager resource is available to run a plate and multiple plates are vying for imager time. When more than one plate is scheduled to run on the imager at a single time the scheduling system supports a conflict resolution management system that arbitrates conflicts and reorders schedules dependent on user derived rules.

The imager has the ability to support all common format experiments used in protein crystallization today. The results are all stored in a common database regardless of the experiment type. The imager requires no definition of experiment type. The imager only requires plate type to run all experiment types. Various experiment types are handled automatically without requiring user intervention to setup the imager to accommodate each type. The following protein crystallization experiment types are supported:

Hanging Drop

These experiments can be conducted on a variety of plate type (Linbro (300), VDX, and Neuroprobe to a name a few). The imager allows for multiple drops per deep well and supports automated drop finding for fully automated image acquisition.

Sitting Drop

The imager will support any sitting drop plate on the market today with any well and satellite well configuration that can be made on an SBS format plate. It can support very dense experiment plates 384 and 1536 as well as large format 24, 48 and 96 well plates.

Microbatch

The imager will support all common microbatch plate setup formats without requiring any special purpose fixturing or user intervention to automatically image.

Alternative Formats

The imager also can support sandwich drop experiment types and has provisions built into the nest to accommodate adapter plates necessary to support future experiment types such as chip and micro slide based experiments.

Temperature Range (0° to 40° C.)

The imager can operate across a wide range of environmental conditions that are common to protein crystallization environments in labs today such as fixed humidity, low temperature, and overpressure conditions. The temperature range supported by the imager is 0° to 40° C.

The invention having been thus described, it will be apparent to those skilled in the art that the same may be varied in many ways without departing from the spirit and scope of the invention. For example, while the preferred embodiment of the invention has been described in conjunction with protein crystallization experiments, the imager of the invention can be used with any type of crystallization or precipitation experiment wherein many different conditions must be configured in order to discover optimal parameter values for crystal or precipitate formation. In the claims which follow, "crystallization" will refer to crystallization or precipitation. Any and all such modifications as would be apparent to one skilled in the art are intended to be included within the scope of the following claims.

What is claimed is:

1. An apparatus that automatically captures stores and analyzes images of crystallization experiments contained in a plurality of crystallization plates, comprising:

a plate nest capable of accommodating protein crystallization plates of a plurality of different types, said plates each including a plurality of crystallization wells each including a particular crystallization experiment;

image acquisition optics, including an objective lens and an image capturing device, for focusing an image of a crystallization well positioned under said objective lens and electronically capturing said focused image;

a light source including a bright field illumination device and a dark field illumination device, each of said bright field and dark field illumination devices being independently energized to introduce light into a crystal image well to enable capture of separate bright field and dark field images of said crystal image well by said image acquisition optics;

a nest positioning controller for moving the position of said plate nest with respect to said image acquisition optics to align various selected wells with said objective lens for imaging of the content of said wells;
a database for storing experiment information associated with each of said plurality of crystallization plates, said experiment information including identification of specific crystal forming parameter values, and wherein each of said plurality of crystallization plates is identified in said database by a unique identification code; and
a crystallization imaging controller for controlling crystallization imaging by retrieving said experiment information for each crystallization plate inserted into said apparatus, and controlling said nest positioning controller and said image acquisition optics in accordance with said retrieved experiment information.

2. An apparatus according to claim 1, wherein said crystallization experiments comprise protein crystallization experiments, and said crystallization imaging plates each contain protein samples combined with varying amounts of protein crystallization inducing catalyst material.

3. An apparatus according to claim 1, further comprising a transmitter polarization filter for polarizing light from said light source to a crystal image well to provide a polarized image of said crystal image well for capture by said image acquisition optics.

4. An apparatus according to claim 3, wherein said experiment information includes polarization angle information, and said crystallization imaging controller controls the polarization angle of said transmitter polarization filter in accordance with said polarization angle information that is from the retrieved experiment information.

5. An apparatus according to claim 4, wherein said experiment information includes multiple polarization angles for at least one crystal image well, and said crystallization imaging controller controls said transmitter polarization filter and said image acquisition optics to capture multiple images of said crystal image well in accordance with said multiple polarization angle information that is retrieved.

6. An apparatus according to claim 1, wherein multiple images of individual crystal image wells captured by said image acquisition optics under varying lighting and/or focusing conditions are processed for forming a single fused image containing partial data from at least two of said multiple images.

7. An apparatus according to claim 3, further comprising an image capture device comprising a camera, said image acquisition optics further including a color filter for enabling true color images to be obtained using said camera, and wherein said color filter also functions as an analyzer polarization filter operating in conjunction with said transmitter polarization filter to form a polarization system for allowing polarized light from said crystallization plate to be imaged.

8. An apparatus according to claim 1, wherein said apparatus analyzes light attenuation data from said image acquisition optics for an image well obtained over a predetermined period of time to calculate a turbidity value for said image well.

9. An apparatus according to claim 1, wherein said apparatus analyzes light attenuation data from a turbidity detection light detector for an image well obtained over a predetermined period of time to calculate a turbidity value for said image well.

10. An apparatus according to claim 1, wherein crystallization plates are loaded and unloaded into said plate nest by a robotic plate loader/unloader.

11. An apparatus according to claim 1, wherein said plate nest further comprises an automatic plate centering cam mechanism that aligns a plate inserted into said plate nest into an appropriate alignment position subsequent to insertion of said plate into said plate nest.

12. An apparatus according to claim 1, wherein said plate nest further comprises an automatic plate alignment mechanism that automatically aligns an inserted plate.

13. An apparatus according to claim 1, further comprising an image capture device further comprising a CCD (charge-coupled device) camera, said image acquisition optics further including a color filter for enabling true color images to be obtained using said CCD camera.

14. An apparatus according to claim 1, wherein said nest positioning controller moves said plate nest in X and Y axis directions in a plane perpendicular to said objective lens, and further moves said plate nest in a Z axis direction toward and away from said objective lens, said apparatus further comprising a Z axis pressure sensor for sensing the presence of a crystallization plate against said image acquisition optics and transmitting a signal to said nest positioning controller to cause said nest positioning controller to stop movement of said plate nest toward said objective lens in said Z axis upon detection of the presence of said crystallization plate.

15. An apparatus according to claim 1, wherein said crystallization plates comprise SBS type plates.

16. An apparatus according to claim 1, wherein said crystallization plates comprise Linbro type plates.

17. An apparatus according to claim 1, wherein said bright field illumination device comprises a plurality of light-emitting diodes.

18. An apparatus according to claim 1, wherein said dark field illumination device comprises a plurality of light-emitting diodes.

19. An apparatus that automatically captures, stores and analyzes images of crystallization experiments contained in a plurality of crystallization plates, comprising:
a plate nest capable of accommodating protein crystallization plates of a plurality of different types, said plates each including a plurality of crystallization wells each including a particular crystallization experiment;
image acquisition optics, including an objective lens and an image capturing device, for focusing an image of a crystallization well positioned under said objective lens and electronically capturing said focused image;
a light source including a bright field illumination device and a dark field illumination device, each of said bright field and dark field illumination devices being independently energized to introduce light into a crystal image well to enable capture of separate bright field and dark field images of said crystal image well by said image acquisition optics;
a transmitter polarization filter located between said light source and said plate nest, for polarizing light from said light source at a desired polarization angle;
said image acquisition optics further including an analyzer polarization filter operating in conjunction with said transmitter polarization filter as a polarization system for allowing polarized light from said crystallization plate to be imaged;
wherein multiple images of individual crystal image wells captured by said image acquisition optics under varying lighting and/or focusing conditions are processed for forming a single fused image containing partial data from at least two of said multiple images.

20. An apparatus according to claim 19, wherein said bright field illumination device comprises a plurality of light-emitting diodes.

21. An apparatus according to claim 19, wherein said dark field illumination device comprises a plurality of light-emitting diodes.

22. A method of analyzing images of crystallization experiments contained in a plurality of crystallization wells, comprising the steps of:
    selectively moving a position of a plate nest with respect to image acquisition optics to align various selected wells with an objective lens for imaging contents of the wells, wherein the plate nest accommodates for protein crystallization plates of a plurality of different types, said plates include a plurality of crystallization wells each including a particular crystallization experiment;
    illuminating a plurality of crystallization experiments within said plurality of wells using a bright field illumination device to obtain a bright field illumination of said plates and capturing an image of each of said plurality of wells under bright field illumination;
    illuminating a plurality of crystallization experiments within said plurality of wells using a dark field illumination device to obtain a dark field illumination of said plates and capturing an image of each of said plurality of wells under dark field illumination;
    wherein said image acquisition optics, including an objective lens and an image capturing device, focuses the images of the plurality of wells under the objective lens and electronically captures images of the plurality of wells; and
    processing said images of said plurality of wells under bright and dark field illumination to determine crystallization results of said crystallization experiment.

23. A method as set forth in claim 22, further comprising the steps of illuminating said plurality of crystallization wells using polarized light and capturing images of said plurality of wells under polarized light illumination, and wherein said processing step further comprises processing said polarized light images.

24. A method as set forth in claim 23, wherein said processing step comprises the step of fusing said bright field, dark field, and polarized light images according to a data fusing algorithm.

25. A method as set forth in claim 22, wherein said processing step comprises the step of fusing said bright field and dark field images according to a data fusing algorithm.

* * * * *